United States Patent [19]

Yoshimura et al.

[11] 4,347,317

[45] Aug. 31, 1982

[54] METHOD FOR PRODUCING L-GLUTAMIC ACID BY FERMENTATION

[75] Inventors: Minoru Yoshimura, Kawasaki; Yoshihiro Takenaka, Fujisawa; Shigeho Ikeda; Hiroe Yoshii, both of Yokohama, all of Japan

[73] Assignee: Ajinomoto Company, Incorporated, Tokyo, Japan

[21] Appl. No.: 175,705

[22] Filed: Aug. 6, 1980

[30] Foreign Application Priority Data

Aug. 10, 1979 [JP] Japan ................................ 54-102448

[51] Int. Cl.$^3$ ............................................ C12P 13/14
[52] U.S. Cl. .................................... 435/110; 435/172; 435/840; 435/843
[58] Field of Search ............................... 435/110–112, 435/172

[56] References Cited

FOREIGN PATENT DOCUMENTS 52-38088  3/1977  Japan .................................. 435/110

OTHER PUBLICATIONS

Tosaka et al., Chemical Abstracts 91: 156040c of Japan Kokai 79, 89085 Jul. 14, 1979.

*Primary Examiner*—Lionel M. Shapiro
*Attorney, Agent, or Firm*—Oblon, Fisher, Spivak, McClelland & Maier

[57] ABSTRACT

Mutants of the genus Brevibacterium or Coryne-bacterium resistant to a respiratory inhibitor or ADP phosphorylation inhibitor produced L-glutamic acid in a high yield, when they are cultured aerobically in an aqueous culture medium.

16 Claims, No Drawings

METHOD FOR PRODUCING L-GLUTAMIC ACID BY FERMENTATION

FIELD OF THE INVENTION

This invention relates to a method for producing L-glutamic acid by fermentation.

DESCRIPTION OF THE PRIOR ART

L-Glutamic acid has been produced by fermentation using a microorganism of the genus Brevibacterium or Corynebacterium. Various attempts have been done to improve the productivity of the known glutamic acid producing strains by artificial mutation techniques. Examples of such artificial mutants are mutants of Brevibacterium resistant to S-2-amino-ethyl-cysteine (Japanese Published Unexamined Patent Application No. 126877/1975, mutants of Brevibacterium and Corynebacterium resistant to fluorocitric acid, ketomalonic acid, α-amino-β-hydroxyvaleric acid, DL-threoninehydroxamate, 2-amino-3-phosphopropionic acid or 5-aminolevulinic acid, (Japanese Published Unexamined Patent Application No. 89045/1979), mutants of Brevibacterium and Corynebacterium sensitive to lysozyme (Japanese Published Unexamined Patent Application No. 122794/1979), mutant of Brevibacterium and Corynebacterium having reduced activity of pyruvic acid dehydrogenase (Japanese Published Unexamined Patent Application No. 21762/1980), mutants resistant to glutamic acid or glutamic acid-analogue of Brevibacterium or Corynebacterium (Japnese Published Unexamined Patent Application No. 21763/1980), and mutants of Brevibacteirum resistant to 2,6-pyridine-dicarboxylic acid (Japanese Published Unexamined Patent Application No. 21764/1980).

SUMMARY OF THE INVENTION

It is now found that mutants of the genus Brevibacterium or Corynebacterium resistant to a respiratory inhibitor or ADP phosphorylation inhibitor produce L-glutamic acid in an improved yield.

Now, it is provided a method for producing L-glutamic acid which comprises culturing in an aqueous culture medium a mutant of the genus Brevibacterium or Corynebacterium which is resistant to a resispiratory inhibitor or ADP phosphorylation inhibitor, and recovering L-glutamic acid accumulated in the resulted culture liquid.

DESCRIPTION OF THE PREFERRED EMBODIMENTS

The respiratory inhibitors of this invention inhibit, as is well known, respiration of the microorganisms, and then their growth. The examples of the respiratory inhibitors are malonic acid, potassium cyanid, sodium azide, sodium arsenite.

The ADP phosphorylation inhibitors inhibit the phosphorylation of ADP (adenosine diphosphate) of microorganisms, and production of ATP (adenosine triphosphate), and then their growth. ADP phosphorylation inhibitors include uncouplers, which inhibit coupling reaction in respiratory chain, such as 2,4-dinitrophenol, hydroxylamine and arsenic, and energy trasfer inhibitors, which inhibit energy transferring reaction such as guanidine.

Specimens of the mutants of this invention are:

*Brevibacterium lactofermentum* AJ 11426 (FERM-P 5123, NRRL B-12211), (malonic acid)
*Brevibacterium flavum* AJ 11427 (FERM-P 5124, NRRL B-12203), (malonic acid)
*Corynebacterium glutamicum* AJ 11441 (FERM-P 5138, NRRL B-12210), (malonic acid)
*Brevibacterium lactofermentum* AJ 11428 (FERM-P 5125, NRRL B-12212), (sodium azide)
*Brevibacterium lactofermentum* AJ 11429 (FERM-P 5126, NRRL B-12213), (potassium cyanid)
*Brevibaterium flavum* AJ 11430 (FERM-P 5127, NRRL B-12204), (potassium cyanid)
*Corynebacterium glutamicum* AJ 11431 (FERM-P 5128, NRRL B-12207), (potassium cyanid)
*Brevibacterium lactofermentum* AJ 11432 (FERM-P 5129, NRRL B-12214), (sodium arsenite)
*Brevibacterium lactofermentum* AJ 11433 (FERM-P 5130, NRRL B-12215), (2,4-dinitrophenol)
*Brevibacterium flavum* AJ 11434 (FERM-P 5131, NRRL B-12205), (2,4-dinitrophenol)
*Brevibacterium lactofermentum* AJ 11435 (FERM-P 5132, NRRL B-12216), (hydroxylamine hydrochloride)
*Corynebacterium glutamicum* AJ 11436 (FERM-P 5133, NRRL B-12208), (hydroxylamine hydrochloride)
*Brevibacterium lactofermentum* AJ 11437 (FERM-P 5134, NRRL B-12217), (arsenic)
*Brevibacterium lactofermentum* AJ 11438 (FERM-P 5135, NRRL B-12218), (guanidine)
*Brevibacterium flavum* AJ 11439 (FERM-P 5136, NRRL B-12206), (guanidine)
*Corynebacterium glutamicum* AJ 11440 (FERM-P 5137, NRRL B-12209), (guanidine)

The mutants of *Brevibacterium flavum*, *Brevibacterium lactofermentum* and *Corynebacterium glutamicum* were derived from the parent strains, *Brevibacterium flavum* ATCC 14067, *Brevibacterium lactofermentum* ATCC 13869 and *Corynebacterium glutamicum* ATCC 13032, respectively. *Brevibacterium divaricatum* ATCC 14020, *Brevibacterium saccharoliticum* ATCC 14066, *Corynebacterium acetoacidophilum* ATCC 13870, and other glutamic acid-producing bacteria of the genera Corynebacterium and Brevibacterium can be used as the parent strains.

The parent strains can be mutated to obtain the mutants of this invention by a conventional manner such as UV-radiation X-ray radiation, exposure to a mutagen. For instance, the parent strain is mutated by exposing to 250 μg/ml N-nitro-N'-methyl-N-nitrosoguanidine at 30° C. fof 20 minutes.

Inhibitory action to the growth of the mutants of this invention and their parents in the presence of the respective inhibitors to which the mutants resist was tested and the results are shown in Tables 1, 2 and 3. As can be seen in Tables 1, 2 and 3, the growth of the mutants of this invention was less inhibited than that of their parents by the inhibitors.

The determination of growth was performed by the following way; the medium containing 1 g/dl yeast extract, 1 g/dl peptone, 0.5 g/dl sodium chloride and 2 g/dl agar of pH 7.0 was sterilized at 120° C. for 15 minutes, and was poured into plates. The plates were inoculated with the microorganisms, which had been cultured on meat extract agar slant for 24 hours and had been suspended into sterilized water. The inoculum size was $10^5 \sim 10^6$ cells per plate. A paper disk containing the amount of inhibitor shown in each Table was placed on each plate. Growth around the paper disk was observed after 16 to 48 hours incubation of the plates at 30° C.

In Tables "++", "+" and "−" show that good growth, poor growth and scarce growth were observed around the disk, respectively.

TABLE 1

| inhibitor in disk(mg/ml) | Growth | | | | | |
|---|---|---|---|---|---|---|
| malonic acid | ATCC 13869 | AJ 11426 | ATCC 14067 | AJ 11427 | ATCC 13032 | AJ 11441 |
| 1 | ++ | ++ | ++ | ++ | + | + |
| 3 | ± | ++ | ± | ++ | − | + |
| 5 | − | + | − | + | − | + |
| 10 | − | + | − | − | − | − |
| KCN | ATCC 13869 | AJ 1429 | ATCC 14067 | AJ 11430 | ATCC 13032 | AJ 11431 |
| 0.1 | + | ++ | + | ++ | + | + |
| 0.3 | ± | + | + | ++ | ± | + |
| 0.5 | − | + | − | + | − | + |
| 0.8 | − | − | − | − | − | − |
| NaN₃ | ATCC 13869 | AJ 11428 | | | | |
| 0.01 | ± | + | | | | |
| 0.05 | − | + | | | | |
| 0.1 | − | − | | | | |
| 0.5 | − | − | | | | |
| Na₃AsO₃ | ATCC 13869 | AJ 11432 | | | | |
| 0.5 | ++ | +++ | | | | |
| 1.0 | − | ++ | | | | |
| 5.0 | − | + | | | | |
| 10 | − | − | | | | |

TABLE 2

| 2,4-Dinitro phenol (mg/ml) | Growth | | | | Hydroxylamine HCl(mg/ml) | Growth | | | | Arsenic (mg/dl) | Growth | |
|---|---|---|---|---|---|---|---|---|---|---|---|---|
| | ATCC 13869 | AJ 11433 | ATCC 14067 | AJ 11434 | | ATCC 13869 | AJ 11435 | ATCC 13032 | AJ 11436 | | ATCC 13869 | AJ 11437 |
| 0.1 | ++ | ++ | ++ | ++ | 0.5 | + | ++ | ++ | ++ | 1 | ++ | ++ |
| 0.5 | + | ++ | ± | ++ | 1.0 | − | ++ | + | ++ | 3 | + | ++ |
| 0.8 | − | + | + | + | 3.0 | − | + | − | + | 5 | − | + |
| 1.0 | − | − | − | − | 5.0 | − | − | − | − | 10 | − | + |

TABLE 3

| Guanidine (mg/ml) | Growth | | | | | |
|---|---|---|---|---|---|---|
| | ATCC 13869 | AJ 11438 | ATCC 14067 | AJ 11439 | ATCC 13032 | AJ 11440 |
| 1 | ++ | ++ | ++ | ++ | + | + |
| 3 | − | ++ | − | ++ | − | + |
| 5 | − | + | − | + | − | − |
| 10 | − | − | − | − | − | − |

The effect of respiratory inhibitor on NADH oxidation of the mutants resistant to respiratory inhibitor and their parents was tested, and the results are shown in Table 4.

NADH oxidation activity was determined by the following manner: Ten ml batches of reaction mixture containing 500 μmoles of phosphate buffer (pH 7.5), 6 μmoles of NADH, a certain volume of cell extract of the test strain and the amount of respiratory inhibitor shown in Table 4 were kept airtight in vessels having oxygen sensor "Beckman model 777", stirred, and held at 32° C. NADH oxidation activity was determined based on the decreasing rate of the partial pressure of oxygen, It was observed that the NADA oxidation activity of AJ 11429, AJ 11430 and AJ 11431 was less reduced by the inhibitors shown in Table 4 than that of their parents.

TABLE 4

| Inhibitor added | conc. (mg/ml) | Relative activity of NADH oxidation | | | | | |
|---|---|---|---|---|---|---|---|
| | | ATCC 13869 | AJ 11429 | ATCC 14067 | AJ 11430 | ATCC 13032 | AJ 11431 |
| malonic acid | 5 | 40 | 70 | 35 | 75 | 20 | 75 |
| KCN | 0.5 | 0 | 85 | 0 | 75 | 0 | 65 |
| NaN₃ | 0.05 | 0 | 50 | 0 | 60 | 0 | 75 |
| Na₃AsO₃ | 1.0 | 15 | 90 | 25 | 95 | 10 | 80 |
| none | — | 100 | 100 | 100 | 100 | 100 | 100 |

Respiration activity and ADP phosphorylation activity of the mutant resistant to ADP phosphorylation inhibitor and their parent were determined in the presence of uncoupler (Table 5) or energy transfer inhibitor (Table 6).

Determination of respiration activity and ADP phosphorylation activity was carried out as follows:

RESPIRATION ACTIVITY

Test strains were cultured for 20 hours in a medium containing, per milliliter, 36 mg glucose, 2 mg urea, 1 mg $KH_2PO_4$, 0.4 mg $MgSO_4.7H_2O$, 10 μg $FeSO_4.7H_2O$, 8 μg $MnSO_4.4H_2O$, 5 μl soybean acid-hydrolysate, 0.1 μg thiamine.HCl, and 0.0025 μg biotin, Cells in the resulted culture liquids were harvested, washed twice with 0.5% NaCl, and suspended in 1/15 M phosphate buffer of pH 7.5. The cell suspension was shaken at 28° C. for 3 hours, and 0.5 ml of the resting cell suspension was put into 2 ml of a reaction mixture containing 100 μmoles of phosphate buffer of pH 7.5, 100 μmoles of glucose and the amount of the inhibitor shown in Table 5 or 6. The reaction mixture was held at 32° C. for 3 hours, and oxygen uptake was measured with warburg manometer.

ADP PHOSPHORYLATION ACTIVITY

The resting cells mentioned above were dried at a room temperature and dried further in a phosphorus pentoxide desiccator under a vacuum overnight. Fifty mg of the dried cells were put into 2 ml of a reaction mixture containing 10 μmoles ADP, 200 μmoles glucose 250 μmoles phosphate buffer, 5 μmoles $MgCl_2.6H_2O$ and the amount of the inhibitor shown in Table 5 or 6. The reaction mixture was held at 30° C. for 3 hours, and then heated in boiling water for 3 minutes.

ATP formed in the reaction mixture was determined colorimetrically.

TABLE 5

| Unconpler added | conc. (mg/ml) | Activity determined | Relative activity | | | | | |
|---|---|---|---|---|---|---|---|---|
| | | | ATCC 13869 | AJ 11433 | ATCC 14067 | AJ 11434 | ATCC 13032 | AJ 11436 |
| 2,4-dinitrophenol | 0.5 | repiration | 125 | 160 | 145 | 145 | 135 | 140 |
| | | ADP phosphorylation | 0 | 65 | 0 | 70 | 0 | 50 |
| hydroxylamine | 1.0 | respiration | 130 | 175 | 120 | 150 | 135 | 160 |
| | | ADP phosphorylation | 0 | 50 | 0 | 65 | 0 | 45 |
| arsenic | 5.0 | respiration | 130 | 160 | 145 | 160 | 140 | 160 |
| | | ADP Phosphorylation | 0 | 50 | 0 | 70 | 0 | 45 |
| none | — | repiration | 100 | 100 | 100 | 100 | 100 | 100 |
| | | ADP phosphorylation | 100 | 100 | 100 | 100 | 100 | 100 |

TABLE 6

| Inhibitor | conc. (mg/ml) | Activity determined | Relative activity | | | | | |
|---|---|---|---|---|---|---|---|---|
| | | | ATCC 13869 | AJ 11438 | ATCC 14067 | AJ 11439 | ATCC 13032 | AJ 11440 |
| guanidine | 3 | respiration | 100 | 110 | 100 | 110 | 100 | 100 |
| | | ADP phosphorylation | 0 | 85 | 15 | 80 | 10 | 75 |
| none | — | respiration | 100 | 100 | 100 | 100 | 100 | 100 |
| | | ADP phosphorylation | 100 | 100 | 100 | 100 | 100 | 100 |

From these experiments, it was observed that ADP phosphorylation activity of both of the mutants resistant to uncoupler and mutant resistant to energy transfer inhibitor was less decreased by uncoupler or energy transfer inhibitor than that of their parents.

The mutants of this invention are cultured to produce L-glutamic acid by conventional manner. Namely, the cultivation is carried out under an aerobic condition at a temperature in the range from 30° C. to 40° C. The culture medium employed in this invention contains carbon sources, nitrogen sources and inorganic ions as in conventional medium.

Preferred carbon sources are carbohydrates (sucrose, glucose, fructose and crude materials containing the carbohydrates such as cane molasses beet molasses and starch hydrolyzate), acetic acid, and ethanol. Most preferred nitrogen sources are urea, gaseous ammonia and aqueous ammonia.

L-Glutamic acid thus accumulated in the resulted culture liquid can be recovered also by conventional manner.

EXAMPLE 1

Twenty milliliter batches of a culture medium containing, per milliliter, 36 mg glucose, 2 mg urea, 1 mg $KH_2PO_4$, 0.4 mg $MgSO_4.7H_2O$, 10 μg $FeSO_4.7H_2O$, 8 μg $MnSO_4.4H_2O$, 0.1 μg thiamine.HCl, 0.0025 μg biotin and 5 μl soy protein hydrolyzate, were placed in 500 ml shaking flasks, and sterilized at 115° C. for 10 minutes.

The microorganisms listed in Table 7 below were inoculated in the culture media and cultured at 31.5° C. with shaking. During the cultivation, a small portion of urea solution (containing 450 mg/ml urea) was fed to the fermentation media to maintain the pH of the fermentation media at from 6.5 to 8.0.

After 30 hours' cultivation, the amounts of L-glutamic acid shown in Table 7 were accumulated.

EXAMPLE 2

An aqueous medium was prepared to contain, per milliliter, 100 mg (as sugar) of cane molasses, 1.0 mg $KH_2PO_4$, 1.0 mg $MgSO_4.7H_2O$, and 0.1 μg thiamine.HCl, adjust to pH 7.0, 30 ml batches of the medium were placed in 500 ml flasks and heated to sterilize.

The microorganisms listed in Table 8 were inoculated in the media and cultured at 31.5° C. with shaking. During the cultivation, an urea solution containing 400 mg/ml urea was fed in the medium so as to maintain the pH of the medium at 6.5~8.0. When the optical density at 562 mμ of a 26 times dilution of the culture medium reached 0.3, 0.5 mg/ml polyoxyethylenesorbitanmonopalmitate were added to the medium.

After 36 hours' of the cultivation, the amounts of L-glutamic acid shown in Table 8 were accumulated.

TABLE 7

| Microorganism tested | L-Glutamic acid accumulated (g/l) |
|---|---|
| ATCC 13869 | 16.2 |
| ATCC 14067 | 15.0 |
| ATCC 13032 | 15.5 |
| AJ 11426 | 17.5 |
| AJ 11427 | 17.0 |
| AJ 11428 | 17.8 |
| AJ 11429 | 17.8 |
| AJ 11430 | 18.2 |
| AJ 11431 | 17.5 |
| AJ 11432 | 18.0 |
| AJ 11433 | 17.5 |
| AJ 11434 | 17.0 |
| AJ 11435 | 18.0 |
| AJ 11436 | 17.2 |
| AJ 11437 | 16.9 |
| AJ 11438 | 18.0 |
| AJ 11439 | 18.0 |
| AJ 11440 | 17.5 |
| AJ 11441 | 17.8 |

TABLE 8

| microorganism tested | L-Glutamic acid accumulated (g/l) |
| --- | --- |
| AJ 11426 | 52.0 |
| AJ 11427 | 49.5 |
| AJ 11429 | 51.5 |
| AJ 11430 | 50.3 |
| AJ 11431 | 51.0 |
| AJ 11433 | 50.9 |
| AJ 11434 | 50.3 |
| AJ 11435 | 51.5 |
| AJ 11436 | 50.8 |
| AJ 11438 | 52.9 |
| AJ 11439 | 52.0 |
| AJ 11440 | 52.5 |
| AJ 11441 | 50.8 |

What is claimed as new and intended to be covered by Letters Patent is:

1. A method for producing L-glutamic acid by fermentation which comprises aerobically culturing in aqueous culture medium a mutant of the genus Brevibacterium or Corynebacterium of which ADP phosphorylation is less inhibited than its parent strain by ADP phosphorylation inhibition, and recovering L-glutamic acid accumulated in the resulting culture liquid, wherein the mutant is selected from the group consisting of:

Corynebacterium glutamicum NRRL B-12210
Brevibacterium lactofermentum NRRL B-12212
Brevibacterium lactofermentum NRRL B-12213
Brevibacterium flavum NRRL B-12204
Corynebacterium glutamicum NRRL B-12207
Brevibacterium lactofermentum NRRL B-12214
Brevibacterium lactofermentum NRRL B-12215
Brevibacterium flavum NRRL B-12205
Brevibacterium lactofermentum NRRL B-12216
Corynebacterium glutamicum NRRL B-12208
Brevibacterium lactofermentum NRRL B-12217
Brevibacterium lactofermentum NRRL B-12218
Brevibacterium flavum NRRL B-12206
Corynebacterium glutamicum NRRL B-12209.

2. The method of claim 1 wherein said mutant is resistant to sodium azide, potassium cyanid, sodium arsenite, 2,4-dinitrophenol, hydroxylamine hydrochloride, arsenic or guanidine.

3. The method of claim 1, wherein the mutant is Brevibacterium lactofermentum NRRL B-12212 which is resistant to sodium azide.

4. The method of claim 1, wherein the mutant is Brevibacterium lactofermentum NRRL B-12213 which is resistant to potassium cyanid.

5. The method of claim 1, wherein the mutant is Brevibacterium flavum NRRL B-12204 which is resistant to potassium cyanid.

6. The method of claim 1, wherein the mutant is Brevibacterium lactofermentum NRRL B-12214 which is resistant to sodium arsenite.

7. The method of claim 1, wherein the mutant is Brevibacterium lactofermentum NRRL B-12215 which is resistant to 2,4-dinitrophenol.

8. The method of claim 1, wherein the mutant is Brevibacterium flavum NRRL B-12205 which is resistant to 2,4-dinitrophenol.

9. The method of claim 1, wherein the mutant is Brevibacterium lactofermentum NRRL B-12216 which is resistant to hydroxylamine hydrochloride.

10. The method of claim 1, wherein the mutant is Brevibacterium lactofermentum NRRL B-12217 which is resistant to arsenic.

11. The method of claim 1, wherein the mutant is Brevibacterium lactofermentum NRRL B-12218 which is resistant to guanidine.

12. The method of claim 1, wherein the mutant is Brevibacterium flavum NRRL B-12206 which is resistant to guanidine.

13. The method of claim 1, wherein the mutant is Corynebacterium glutamicum NRRL B-12210 which is resistant to malonic acid.

14. The method of claim 1, wherein the mutant is Corynebacterium glutamicum NRRL B-12207 which is resistant to potassium cyanid.

15. The method of claim 1, wherein the mutant is Corynebacterium glutamicum NRRL B-12208 which is resistant to hydroxylamine hydrochloride.

16. The method of claim 1, wherein the mutant is Corynebacterium glutamicum NRRL B-12209 which is resistant to guanidine.

* * * * *